United States Patent [19]

Spivack

[11] 4,143,028

[45] Mar. 6, 1979

[54] ALKYLATED 1,1'-BIPHENYL-2,2'-DIYL PHOSPHONITES AND STABILIZED COMPOSITIONS

[75] Inventor: John D. Spivack, Spring Valley, N.Y.

[73] Assignee: Ciba-Geigy Corporation, Ardsley, N.Y.

[21] Appl. No.: 857,167

[22] Filed: Dec. 5, 1977

[51] Int. Cl.$^2$ .............................................. C08K 5/53
[52] U.S. Cl. .......................... 260/45.95 D; 260/23 H; 260/927 R; 260/936; 260/45.95 C
[58] Field of Search ............... 260/45.8 R, 927 R, 936

[56] References Cited

U.S. PATENT DOCUMENTS

| 2,151,680 | 3/1939 | Britton et al. | 260/927 R |
|---|---|---|---|
| 3,264,324 | 8/1966 | Gould et al. | 260/927 R |
| 3,270,092 | 8/1966 | Harwood | 260/937 |
| 3,297,631 | 1/1967 | Bown et al. | 260/936 |
| 3,702,878 | 11/1972 | Saito | 260/936 |
| 3,796,684 | 3/1974 | Dever et al. | 260/45.8 R |
| 3,819,748 | 6/1974 | Dulog et al. | 260/927 R |
| 3,848,030 | 11/1974 | Viterbo et al. | 260/936 |

*Primary Examiner*—Donald E. Czaja
*Assistant Examiner*—R. A. White
*Attorney, Agent, or Firm*—Vincent J. Cavalieri; Joseph F. DiPrima

[57] ABSTRACT

Alkylated 1,1'-biphenyl-2,2'-diyl phosphonites are prepared by reacting alkylated 2,2'-dihydroxybiphenylene with dichloroaryl or dichloroalkyl phosphine in an organic solvent. Said phosphonites are useful as stabilizers of organic polymers and lubricating oils, especially as process stabilizers for polyolefins.

12 Claims, No Drawings

ALKYLATED 1,1'-BIPHENYL-2,2'-DIYL PHOSPHONITES AND STABILIZED COMPOSITIONS

BACKGROUND OF THE INVENTION

Organic polymeric materials such as plastics and resins and lubricating and mineral oil are subject to thermal, oxidative and photodegradation. A great variety of stabilizers are known in the art for stabilizing various substrates. Their effectiveness varies depending on the causes of degradation and the substrate stabilized. During the course of this work it was discovered that stabilizers that are very effective long term antioxidants are relatively poor process stabilizers which require stabilization of the substrate, against thermal degradation for a short time but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphonites of this invention possess an unusual combination of desirable properties as compared to the prior art phosphonites which makes these compounds particularly effective and useful as stabilizers. The prior art discloses unhindered 2,2'-biphenylenephenylphosphonite (J. Am.Chem.Soc.88, 168-9 (1966) and 2,2'-methylene bis(dialkylphenyl) phenylphosphonites (U.S. Pat. No. 3,297,631), the latter being said to inhibit oxidative degradation of polyolefins, especially polypropylene. However the phosphonites of this invention are much more effective, especially as process stabilizers of polyolefins and other substrates.

DETAILED DISCLOSURE

This invention is directed to alkylated 1,1'-biphenyl-2,2'-diylphosphonites and to polymeric and non-polymeric organic materials stabilized with said phosphonites. More specifically the phosphonites of this invention can be represented by the formula

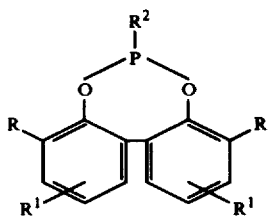

wherein
R is an alkyl group of 1 to 18 carbon atoms,
$R^1$ is hydrogen or an alkyl group of 1 to 18 carbon atoms, and
$R^2$ is an alkyl group of 1 to 18 carbon atoms, phenyl, phenyl substituted with up to 3 alkyl groups each having 1 to 8 carbon atoms, or a group of the formulae

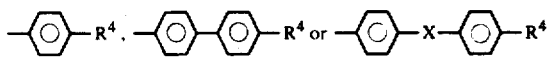

where $R^4$ is of the formula

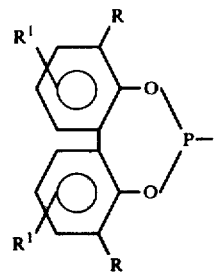

and X is O or S.

The R groups are preferably straight-chain or branched alkyl with 1-8 carbon atoms, such as methyl, ethyl, n-propyl, iso-propyl, n-butyl, sec.-butyl, tert.-butyl, 2-ethylhexyl and n-octyl and tert-octyl. α-Branched alkyl radicals with 3-8 carbon atoms are more preferred. The groups tert-butyl and tert-octyl are especially preferred. Also especially preferred is for the $R^1$ group to be in the para position to oxygen, particularly if $R^1$ is a tert.-alkyl.

Although $R^1$ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms.

The group $R^2$ can be alkyl of 1 to 18 carbon atoms, such as methyl, ethyl, butyl, hexyl, heptyl, octyl, decyl, dodecyl, hexadecyl, octadecyl and the like; or it can be phenyl or alkyl substituted phenyl, such as tolyl, xylyl, mesitylyl, ethylphenyl, butylphenyl, 3,5-dibutylphenyl, p-octylphenyl, 3,5-dioctylphenyl and the like or a group

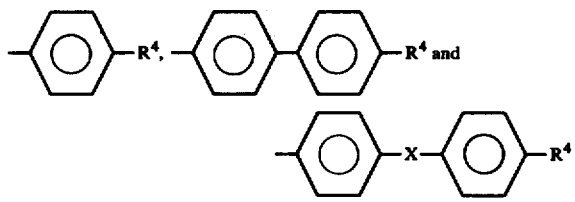

where $R^5$ is a 2,2'-biphenylene phosphonite moiety as represented by the formula hereinabove and X=O and S. Preferably $R^2$ is phenyl or alkyl substituted phenyl where alkyl groups have 1 to 3 carbon atoms.

The alkylated 1,1'-biphenyl-2,2'-diyl phosphonites of this invention can be prepared by reacting an alkylated 2,2'-dihydroxybiphenylene with dichlorophenylphosphine, where the phenyl is either unsubstituted or substituted as defined above, in a solvent. The solvent is preferably aromatic, such as benzene, toluene, xylene and the like. The reaction can be carried out either in the absence or presence of a proton acceptor such as a tertiary amine, for example, triethylamine, pyridine, N,N- dimethylaniline, and the like. A reaction temperature from room temperature to the reflux temperature of the reaction solvent may be employed.

The compounds of this invention are effectively light stabilizers and/or antioxidants in a wide range of organic polymers. Polymers which can be stabilized include:
  1. Polymers which are derived from mono- or diolefins, e.g., polyethylene which can optionally be crosslinked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene, with acrylic or methacrylic acid.
4. Polystyrene.
5. Copolymers of styrene and of α-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from α,β-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas.
15. Polycarbonates.
16. Polysulphones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Cross-linked polymers which are derived from aldehydes on the one hand and from phenols, ureas and melamines on the other, for example phenol/formaldehyde, urea/formaldehyde and melamine/formaldehyde resins.
20. Alkyd resins, for example glycerol/phthalic acid resins and mixtures thereof with melamine/formaldehyde resins.
21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

Compounds of this invention are particularly effective in stabilizing organic materials such as plastics, polymers, resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methylpentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers. Also stabilized are polyurethanes, polycarbonates, polyamides such as nylon 6, 6/6 and the like as well as copolyamides and polysulfones.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutylene-terephthalates, polycarbonates, natural rubber, synthetic rubber such as SBR. While many compounds which have been used as process stabilizers are sufficiently effective as process stabilizers for polyolefins only in the presence of costabilizers such as phenolic antioxidants, compounds of this invention are effective in the absence of phenolic antioxidants.

Many of the compounds of this invention combine process stabilizing properties with the ability to confer light stability on the polymer. This is particularly important for polymer fibers where processing temperatures are among the highest and where stability to actinic light is a prime requirement. A particularly important property for stabilizers which are trivalent phosphorus esters is their non-hygroscopicity and resistance to hydrolysis in the presence of moisture in the atmosphere during ambient storage. Hygroscopicity frequently results in difficulty in incorporating the process stabilizer uniformly into the polymer causing stickiness and blockage during compounding, while hydrolysis of the phosphorus ester stabilizers during storage frequently results in compounds which are less effective.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2,6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulphide.

1.4. Alkylidene-bisphenols, such as for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)pentane and ethylene glycol bis-[3,3-bis-(3'-tert.-butyl-4'-hydroxyphenyl)-butyrate].

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenyl)-propionyl)-hydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11 Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol trimethylolethane, trimethylolpropane, trishydroxyethyl isocyanurate and 4-hydroxymethyl-1-phospha-2,6,7-trioxabicyclo[2,2,2]octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane, especially the tetra-bis ester of pentaerythritol.

1.13 Benzylphosphonates, such as, for example, dimethyl 3,5-di-tert.-butyl-4-hydroxybenzyl-phosphonate, diethyl 3,5-di-tert.-butyl-4-hydroxybenzyl-phosphonate, dioctadecyl 3,5-di-tert.-butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and Light-stabilising Agents 2.1. 2-(2'-Hydroxyphenyl)-benzotriazoles, e.g. the 5'-methyl-, 3',5'-di-tert.-butyl-, 5'-tert.-butyl-, 5'-(1,1,3,3-tetramethylbutyl)-, 5-chloro-3',5'-di-tert.butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxycinnamic acid methyl ester or -butyl ester or N-(β-carbomethoxyvinyl)-2-methyl-indoline.

2.7. Sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal Deactivators, e.g. oxanilide, isophthalic acid dihydrazide, sebacic acid-bisphenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri(nonylphenyl) phosphite, trilauryl phosphite, trioctadecyl phosphite, 3,9-isodecyloxy-2,4,8,10-tetraoxa-3,9-diphospha-[5,5]-undecane and tri-(4-hydroxy-3,5-di-tert.butylphenyl) phosphite.

Other additives that can be incorporated in the stabilized compositions are thiosynergists such as dilaurylthiodiproprionate or distearylthiodipropionate, lubricants such as stearyl alcohol fillers, carbon black, asbestos, kaolin, talc, glass fibers, pigments, optical birghteners, flameproofing agents and antistatic agents.

EXAMPLE 1

3,3',5,5'-tetra-tert.-butyl-1,1'-biphenyl-2,2'-diylphenylphosphonite

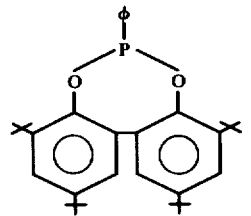

7.12 Grams of dichlorophenylphosphine was added dropwise over 8 minutes at 25° to 30° C. to a solution of 20.2 grams of triethylamine and 16.4 grams of 3,3',5,5'-tetra-tert.-butyl-2,2'-dihydroxy-1,1'-biphenyl in 10 ml of dry benzene. 50 ml additional of dry benzene was added to the resulting thick reaction mixture to facilitate stirring. After stirring for an additional 15 minutes at 30° C. and for four hours at 65° to 70° C., the reaction mixture was filtered free of precipitated triethylamine hydrochloride. The product was isolated from the clear filtrate by removing the volatiles at 0.3 mm at 50° to 60° C. and crystallizing the resulting residue from a mixture of 150 ml acetonitrile and 50 ml of ethyl acetate. After drying, the product was obtained as white crystals melting at 166°-168°.

EXAMPLE 2

3,3',5,5'-tetra-tert.-amyl-1,1'-biphenyl-2,2-diyl phenylphosphonite

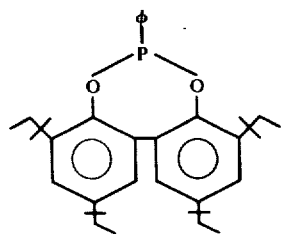

This compound was made by substantially the same procedure as given in Example 1, yielding the desired product as white crystals melting at 96°–99°.

EXAMPLE 3
3,3',-di-tert.-butyl-5,5'-dimethyl-1,1'-piphenyl-2,2'-diyl

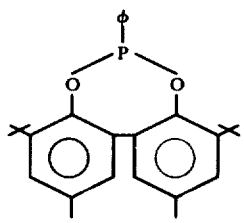

Following the procedure of Example 1, except for employing the appropriate reactants, the above named compound, m.p. 156°–163° C., was obtained.

EXAMPLE 4
3,3',5,5'-tetra-tert.-octyl-1,1'-biphenyl-2,2'-diyl phenylphosphonite

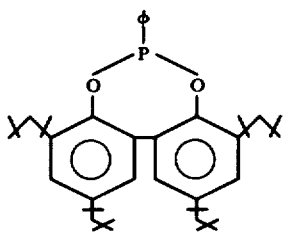

Following the procedure of Example 1, except for employing the appropriate reactants, the above named compound, having m.p. 97°–99° C., was prepared.

EXAMPLES 5–16

Following the procedure of Example 1, except for employing an appropriate phosphonous dichloride and a phenol, the following compounds are prepared where groups R, $R^1$ and $R^2$ refer to Formula I above:

| Ex.No. | R | $R^1$ | $R^2$ |
|---|---|---|---|
| 5 | t-butyl | 4-t-butyl | (2,4,6-trimethylphenyl) |
| 6 | isopropyl | 4-isopropyl | $C_6H_5-$ |
| 7 | methyl | 4-methyl | $C_6H_5-$ |
| 8 | t-butyl | 4-t-butyl | $R^4-\phi-\phi-$ |
| 9 | t-butyl | 4-t-butyl | $R^4-\phi-O-\phi-$ |
| 10 | methyl | 4-t-butyl | $R^4-\phi-$ |
| 11 | t-butyl | 4-t-butyl | $CH_3-$ |
| 12 | t-butyl | 4-methyl | $n-C_{18}H_{37}-$ |
| 13 | t-butyl | 4-octadecyl | $C_6H_5-$ |
| 14 | t-butyl | 4-octyl | ISO-$C_8H_{17}$ (3,5-di-iso-octylphenyl) |
| 15 | t-butyl | 3-methyl | $C_6H_5-$ |
| 16 | t-butyl | t-butyl | $R^4-\phi-S-\phi-$ |

EXAMPLE 17

Processing Stability of Polypropylene at 500° F.

Base Formulation:

| | |
|---|---|
| Profax 6801 | 100 parts |
| Calcium stearate | 0.10 parts |

Stabilizers were solvent blended into polypropylene as solutions in methylene chloride and, after removal of the solvent by evaporation at reduced pressure, the resin was extruded using the following extruder conditions:

| | Temp. | |
|---|---|---|
| | (° F.) | (° C.) |
| Cylinder #1 | 450 | 232 |
| Cylinder #2 | 475 | 246 |
| Cylinder #3 | 500 | 260 |
| Die #1 | 500 | 260 |
| Die #2 | 500 | 260 |
| RPM | 100 | |

During extrusion, the internal extruder pressure was determined using a pressure transducer. After each of the first, third and fifth extrusions, resin pellets were compression molded into 125 mil (3.2mm) thick plaques at 380° F. (193° F.) and specimen yellowness index (Y.I.) determined according to ASTM D1925-63T.

The melt flow rate (MFR) was determined by ASTM method 1238 condition L. The melt flow rate varies directly as the transducer pressure and both are a measure of the molecular weight for a specific type of polymer.

The data is presented in Table I below.

Table I
Process Stability of Polypropylene at 500° F

| Additive | Transducer Pressure (psi) After Extrusion | | | MFR (g/10Min) After Ext.** | | | YI Color After Extrusion*** | | |
|---|---|---|---|---|---|---|---|---|---|
| | 1 | 3 | 5 | 1 | 3 | 5 | 1 | 3 | 5 |
| None | 1095 | 840 | 655 | 0.73 | 2.01 | 4.25 | 4.6 | 6.5 | 7.9 |
| 0.1 Antioxidant A* | 1215 | 1045 | 930 | 0.42 | 1.04 | 1.25 | 6.7 | 8.6 | 10.5 |
| 0.05% Compound of Ex. 1 | 1425 | 1275 | 1110 | 0.22 | 0.31 | 0.51 | 4.6 | 6.1 | 7.0 |
| 0.05% Compound of Ex. 4 | 1380 | 1260 | 1140 | 0.23 | 0.37 | 0.74 | 4.9 | 5.6 | 6.1 |
| 0.1% Antioxidant A | 1470 | 1305 | 1200 | 0.21 | 0.36 | 0.51 | 5.4 | 7.5 | 9.7 |

Table I-continued

| | Process Stability of Polypropylene at 500° F | | | | | | | | |
|---|---|---|---|---|---|---|---|---|---|
| | Transducer Pressure (psi) After Extrusion | | | MFR (g/10Min) After Ext.** | | | YI Color*** After Extrusion | | |
| Additive | 1 | 3 | 5 | 1 | 3 | 5 | 1 | 3 | 5 |
| +0.05% Cpd. of Ex. 1 <br> 0.1% Antioxidant A <br> +0.05% Cpd. of Ex. 4 | 1455 | 1305 | 1155 | 0.23 | 0.36 | 0.70 | 5.4 | 6.9 | 9.7 |

*Antioxidant A is pentaerithritol tetrakis -[3-(3',5'-di-tert.-butyl-4'-hydroxyphenyl) propionate] (IRGANOX® 1010)
**Melt flow rate
***Yellowness Index When the above test is carried out with compounds of Examples 3, 7, 12, 13, and 14, similar stabilization effectivness is obtained.

Light stability of the above composition is improved by incorporating therein 0.1% of one of the UV absorbers listed below:

(a) 2(2'-hydroxy-3',5'-di-t-butylphenyl)-5-chlorobenzotriazole
(b) 2-hydroxy-4-methoxy-5-sulfobenzophenone trihydrate
(c) 2-hydroxy-4-n-octoxybenzophenone
(d) [2,2'-thiobis(4-t-octylphenolate)]-n-butylamine nickel II
(e) p-octylphenyl salicylate
(f) 2,2'-dihydroxy-4,4'-dimethoxybenzophenone
(g) 2(2'-hydroxy-5'-methylphenyl)-benzotriazole.
(h) bis(2,2,6,6-tetramethyl-4-piperidyl) sebacate
(i) nickel salt of o-ethyl 3,5-di-tert.-butyl-4-hydroxybenzylphosphonic acid.

EXAMPLE 18

Processing Stability of Polypropylene at 550° F.

Except for increasing the extruder temperature to 550° F., the same procedure and base formulation as in Ex. 17 was used for testing the processing stability of polypropylene at 550° F.

Extruder conditions were as follows:

| | Temp | |
|---|---|---|
| | ° F. | ° C |
| Cylinder 1 | 500 | 260 |
| Cylinder 2 | 525 | 274 |
| Cylinder 3 | 550 | 305 |
| die 1 | 550 | 305 |
| die 2 | 550 | 305 |
| RPM | 110 | |

The data is presented in TABLE II below.

TABLE II

| Additive | Transducer Pressure (psi) After Extrusion | | | MFR (g/10 min) After Extrusion | | | YI Color After Extrusion | | |
|---|---|---|---|---|---|---|---|---|---|
| | 1 | 3 | 5 | 1 | 3 | 5 | 1 | 3 | 5 |
| None | 765 | 360 | 225 | 1.63 | 9.40 | 20.60 | 4.3 | 4.8 | 5.8 |
| 0.1% Antioxidant A | 925 | 670 | 525 | 0.68 | 1.60 | 3.25 | 4.7 | 7.6 | 10.1 |
| 0.1% Compound of Ex. 1 | 1185 | 975 | 855 | 0.22 | 0.48 | 0.88 | 4.0 | 6.6 | 7.8 |
| 0.1% Antioxidant A + 0.05% Compound Ex. 1 | 1165 | 1050 | 945 | 0.16 | 0.35 | 0.66 | 5.1 | 6.2 | 9.2 |

Similar results are obtained when in place of pentaerithritol tetrakis-{3-(3,5-di-t-butyl-4-hydroxyphenyl) propionate} (Antioxidant A) the following antioxidants are used: octadecyl β-(3,5-di-t-butyl-4-hydroxyphenyl)-propionate thiodiglycol-bis-{3-(3,5-di-t-butyl-4-hydroxyphenyl) propionate} N,N'-bis-β-(3,5-di-t-butyl-b 4-hydroxy-phenyl)-propionyl-hydrazine, -di-2-octadecyl 3,5-di-tert-butyl-4-hydroxybenzyl-phosphonate.

EXAMPLE 19

Stabilization of Polyethylene Terephthalate

1% of the compound of Example 1 is added as a stabilizer to molten polyethylene terephthalate at 270° C. while stirring under a nitrogen atmosphere. The resulting formulated polymer is ground with solid carbon dioxide until the particle size is less than 100 microns in diameter. The temperature at which the onset of oxidation takes place is determined as follows:

About 1 milligram of the polyester powder, as prepared above, is charged into the chamber of the Perkin-Elmer Differential Scanning Calorimeter and heated under nitrogen until a temperature of 225° C. is reached. The nitrogen flow is stopped and oxygen is introduced at a rate of 15 ml per minute while heating at a rate of 1 degree per minute until the oxidation exotherm is recorded. The oxidation temperature of the formulated powder is thus determined to be higher than the base polyester powder without the stabilizer. The higher oxidation temperature provided by the stabilizer clearly shows the marked improvement in inhibition of oxidation. The color of the stabilized polyester is also improved compared to that without the additive.

EXAMPLE 20

Stabilization of Lexan Polycarbonate

Lexan polycarbonate was formulated by mixing the base resin in a Waring Blender with 0.1% of the compound of Example 1, the base resin also containing 0.1% of octadecyl β-(3,5-di-t-butyl-4-hydroxyphenyl) propionate. The formulated resin was compression molded, cut into chips and charged into the melt index apparatus. After maintaining at 350° C. for 30 minutes a sample was removed compressed into plaques and examined for color. The sample containing both stabilizers was much lighter in color than that containing only octadecyl β-(3,5-di-t-butyl-4-hydroxyphenyl) propionate.

EXAMPLE 21

Stabilization of Acrylonitrile - Butadiene - Styrene (ABS)

ABS resin was prepared by heating at 80° C. for 7.5 hours the following formulations
Resin A:

| butadiene | 10 parts |
|---|---|
| acrylonitrile | 24 |
| styrene | 65.8 |
| 2,2'-azobisisobutyronitrile | 0.1 |
| | 99.9 parts |

Resin B: This resin was prepared in the same resin as Resin A except that it contained additionally 0.25% of the compound of Example 1.

The oxidation temperature of each of the resins was determined by Differential Scanning Calorimetry (DSC) employing the following procedure:

10 mg was charged to the DSC pan and heated from ambient temperature at a rate of 20° C./minute in an oxygen stream flowing at the rate of 250 ml/minute. The temperature at which an exotherm was observed for each of the resins was recorded.

| | DSC Temp. (° C) To Exotherm |
|---|---|
| Resin A | 185 |
| Resin B | 192 |

These results show that oxidation of the ABS resin is delayed when the compound of Example 1 is incorporated therein.

EXAMPLE 22

Processing Stability of HMW-HDPE

The high molecular weight-high density polyethylene used was designated as Union Carbide 10780-64A, to which were added the stabilizers dissolved in methylene chloride by solvent blending an amount sufficient to give the desired concentration of the stabilizer after evaporation of the solvent at reduced pressures. The formulated resin was then extruded at 600° F. (316° C.) and the melt flow rate (MFR) and yellowness index (YI) was determined by ASTM D1238-65T condition and ASTM D1925-63T respectively. The results are shown in Table III below.

Table III

| Processing Stability of High Molecular Weight High Density Polyethylene at 600° F (316° C) | | | | | | |
|---|---|---|---|---|---|---|
| | MFR (g/10 min) After Extrusion | | | YI Color After Extrusion | | |
| Additive | 1 | 3 | 5 | 1 | 3 | 5 |
| None | 3.8 | 3.1 | 2.9 | −0.7 | 1.2 | 1.9 |
| 0.1% Antioxidant B** | 4.4 | 4.1 | 4.0 | −1.2 | 2.5 | 3.5 |
| 0.1% Antioxidant A* | 4.4 | 4.1 | 4.2 | −0.8 | 5.7 | 9.5 |
| 0.05% Antioxidant A 0.05% Compound Ex. 1 | 4.9 | 4.3 | 4.1 | −4.9 | −2.3 | −1.4 |
| 0.05% Antioxidant B 0.05% Compound Ex. 1 | 4.8 | 3.6 | 3.5 | −5.1 | −3.7 | −3.2 |

*Antioxidant A is as defined in Table I
**Antioxidant B is octadecyl β-(3,5-di-tert.-butyl-4-hydroxy-phenyl) propionate

EXAMPLE 23

The compound of Example 1 is effective in improving the initial color of high density polyethylene (HDPE) in the form of 125 mil thick plaques as shown below:

Base Formulation:

| | Wt. % |
|---|---|
| HDPE (USI-LR-334) | 98.725 |
| $TiO_2$ | 1.0 |
| Antioxidant A | 0.075 |
| Light Stabilizer X | 0.1 |
| Light Stabilizer Y | 0.1 |
| | 100.000 |

Antioxidant A—define above

Light Stabilizer X—bis (2,2,6,6-tetra-methyl-4-piperidyl) sebacate (TINUVIN®770)

Light Stabilizer Y—2-(2'-hydroxy-3',5'-di-tert-amylphenyl)-benzotriazole (TINUVIN®328)

| | Initial Yellowness Index |
|---|---|
| Base formulation | 11.4 |
| Base formulation + 0.075 Compound of Ex. 1 | 6.8 |

What is claimed is:

1. A phosphonite of the formula

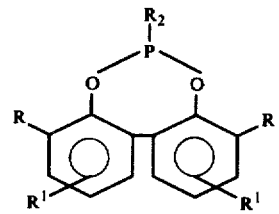

wherein

R is an alkyl group of 1 to 18 carbon atoms, $R^1$ is hydrogen or an alkyl group of 1 to 18 carbon atoms, and $R^2$ is an alkyl group of 1 to 18 carbon atoms, phenyl, phenyl substituted with 1 to 3 alkyl groups each having 1 to 8 carbon atoms, or a group of formulae

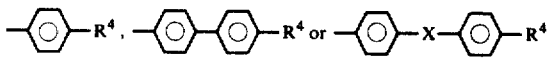

where $R^4$ is of the formula

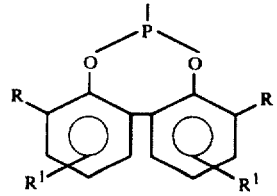

and

X is oxygen or sulfur,

2. A compound of claim 1 wherein

R groups are α-branched alkyl radicals with 3 to 8 carbon atoms,

R¹ groups are alkyl radicals of 1 to 8 carbon atoms, and

R² is methyl, phenyl or an alkyl substituted phenyl, where the alkyl substituent has 1 to 8 carbon atoms.

3. A compound of claim 2 wherein R is tert-butyl, tert-amyl or tert-octyl.

4. A compound of claim 3 wherein R² is phenyl.

5. The compound of claim 1 which is 3,3',5,5'-tetra-tert.-butyl-1,1'-biphenyl-2,2'-diyl phenylphosphonite.

6. The compound of claim 1 which is 3,3',5,5'-tetra-tert.-amyl-1,1'-biphenyl-2,2'-diyl phenylphosphonite.

7. The compound of claim 1 which is 3,3',5,5'-tetra-tert.-octyl-1,1'-biphenyl-2,2'-diyl phenylphosphonite.

8. A composition of matter comprising an organic material subject to oxidative, thermal and actinic degradation stabilized with a compound of claim 1.

9. A composition of matter of claim 8 wherein the organic material is a synthetic polymer.

10. A composition of claim 9 wherein the polymer is an olefin homopolymer or copolymer.

11. An olefin homopolymer or copolymer stabilized with a compound of claim 3.

12. A composition of claim 9 wherein an ethylene or propylene homopolymer or copolymer is stabilized with 3,3',5,5'-tetra-tert.-butyl-1,1'-biphenyl-2,2'-diyl phenylphosphonite or 3,3',5,5'-tetra-tert.-amyl-1,1'-biphenyl-2,2'-diyl phenylphosphonite.

* * * * *